United States Patent
Van Den Enden

(10) Patent No.: US 10,849,303 B2
(45) Date of Patent: Dec. 1, 2020

(54) FERTILISATION INDEPENDENT FRUIT FORMATION IN EGGPLANT

(71) Applicant: RIJK ZWAAN ZAADTEELT EN ZAADHANDEL B.V., De Lier (NL)

(72) Inventor: Johannes Henricus Jacobus Van Den Enden, De Lier (NL)

(73) Assignee: RIJK ZWAAN ZAADTEELT EN ZAADHANDEL B.V., De Lier (NL)

(*) Notice: Subject to any disclaimer, the term of this patent is extended or adjusted under 35 U.S.C. 154(b) by 567 days.

(21) Appl. No.: 15/168,917

(22) Filed: May 31, 2016

(65) Prior Publication Data

US 2016/0272998 A1 Sep. 22, 2016

Related U.S. Application Data

(63) Continuation-in-part of application No. PCT/EP2014/077334, filed on Dec. 11, 2014.

(30) Foreign Application Priority Data

Dec. 12, 2013 (EP) .................................... 13196955

(51) Int. Cl.
| | |
|---|---|
| A01H 6/82 | (2018.01) |
| A01H 1/02 | (2006.01) |
| A01H 5/08 | (2018.01) |
| A01H 1/00 | (2006.01) |

(52) U.S. Cl.
CPC ............... A01H 6/826 (2018.05); A01H 1/02 (2013.01); A01H 1/00 (2013.01); A01H 5/08 (2013.01)

(58) Field of Classification Search
None
See application file for complete search history.

(56) References Cited

U.S. PATENT DOCUMENTS

| | | | |
|---|---|---|---|
| 6,483,012 B1 | 11/2002 | Spena et al. | |
| 2011/0061121 A1 | 3/2011 | Dirks et al. | |

FOREIGN PATENT DOCUMENTS

| | | | | |
|---|---|---|---|---|
| CN | 102668977 | | 9/2012 | |
| IN | 217/KOL/2012 A | * | 4/2012 | ............ C09B 61/00 |
| WO | 98/28430 | | 7/1998 | |
| WO | 2009/095266 | | 8/2009 | |

OTHER PUBLICATIONS

Rotino et al (1997, "Genetic Engineering of Parthenocarpic Plants". Nature biotechnology: 15 1398-1401).*
Saito et al (2009, "A Novel Source of Cytoplasmic Male Sterility and a Fertility Restoration Gene in Eggplant (*Solanum melongena* L.) Lines". J. Japan. Soc. Hort. Sic. 78(4): 425-430).*
Khan et al. Plant Breeding 130(2): 256-260 (Apr. 2011).*
Khan et al. Journal of the Japanese Society of Horticultural Science 79(4): 348-353 (2010).*
Khan et al. Journal of Horticultural Science & Biotechnology 84(1): 92-96 (2009).*
Chinese First Office Action dated Jun. 5, 2017, which issued during prosecution Chinese Application No. CN201480067513.
International Search Report and Written Opinion of the International Searching Authority dated Jan. 23, 2015, which issued during prosecution of International Application No. PCT/EP2014/077334.
Khan, et al. "Pollen and seed fertility of the male fertile lines having the fertility restorer gene in three CMS systems of eggplant" Scientia Horticulturae, Jun. 2013, 157:39-44.
Kikuchi, et al. "Stability of fruit set of newly selected parthenocarpic eggplant lines" Scientia Horticulturae, Dec. 2007, 115(2):111-116.

* cited by examiner

*Primary Examiner* — David T Fox
(74) *Attorney, Agent, or Firm* — Duane Morris LLP; Thomas J. Kowalski; Deborah L. Lu

(57) ABSTRACT

The present invention relates to an eggplant seed that is capable of growing into a plant that is cytoplasmic male sterile and can produce eggplant fruits without fertilization. The present invention also relates to a plant produced by growing the eggplant. The invention further relates to methods for producing the seedless eggplant fruits.

6 Claims, 1 Drawing Sheet

A. Flowers with normally opening anthers of non-CMS plants. B. Flowers with deformed non-opening anthers of CMS plants.

FERTILISATION INDEPENDENT FRUIT FORMATION IN EGGPLANT

RELATED APPLICATIONS AND INCORPORATION BY REFERENCE

This application is a continuation-in-part application of international patent application Serial No. PCT/EP2014/077334 filed 11 Dec. 2014, which published as PCT Publication No. WO 2015/086726 on 18 Jun. 2015, which claims benefit of European patent application Serial No. 13196955.2 filed 12 Dec. 2013.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a seedless eggplant and to a method for producing such a plant.

BACKGROUND OF THE INVENTION

The eggplant or aubergine (*Solanum melongena*) is a member of the Solanaceae plant family and part of the *Solanum* genus which comprises more commercially interesting species such as tomato, potato and pepper. Because of its large, pendulous, purple or white fruit, the eggplant is an important food crop. It has been cultivated in southern and eastern Asian countries since prehistory but is now also grown commonly in the Western world.

The fruit contains numerous small, soft seeds. From a commercial point of view seedlessness is a very desirable trait in edible fruit and vegetables, like the eggplant. The presence of seeds in ready-to-harvest fruits is considered as a negative quality. This is inter alia because seeds can lead to undesired browning of the flesh. Furthermore, seedless fruits are in general more sweet than fruits with seeds. Industrial or domestic applications which require seed removal from the fruits can also benefit strongly from the absence of seeds.

Seedlessness or the absence of seeds can be the result of parthenocarpic fruit formation, where fruits set without fertilization. In certain species parthenocarpic fruit set still requires pollination or another stimulus, in particular spraying the flowers with plant growth regulators, such as gibberellin, auxin and cytokinin. This is termed artificial parthenocarpic fruit formation.

Parthenocarpic fruit formation is not only interesting for obtaining seedless fruits. Unfavourable environmental conditions such as high or low temperatures and drought can hamper normal pollination which leads to poor fruit set and as a consequence yield loss. When fruit formation independent of fertilization or parthenocarpic fruit formation can be harnessed as a trait, it could significantly contribute to an economically more efficient production of eggplant fruits.

In addition to contributing to harvest security, parthenocarpic fruit formation is also important for fruit quality. Parthenocarpic eggplant fruits have been mentioned to have a better flavour (less bitter) as well as a higher dry matter content as compared to seeded eggplant fruits. The higher level of soluble solids is especially important for processing eggplants which are used in industry for paste production. In addition, such fruit can be advantageous for the fresh cut industry which requires firm fruits which are not leaky.

Several parthenocarpic eggplant varieties are known (e.g. Talina, Galine). During winter cultivation of such eggplant varieties fruit production may be hampered by suboptimal environmental conditions. These are usually counteracted by treating flower buds with plant growth regulators. However, these phytohormonal treatments make the production process more expensive due to the cost of both chemicals and labour. The involvement of the plant hormones auxin and gibberellin has been extensively documented although their precise role remains elusive. The application of either auxin or gibberellin to the unfertilised ovule leads in many plant species including eggplant to fruit formation. In practice, these hormones are applied to improve fruit set when greenhouse conditions are suboptimal. Although the application of auxin and gibberellin has some practical value it increases costs and it may lead to irregularities in fruit shape. In addition, the use of hormones is under discussion or prohibited in some countries.

Parthenocarpic fruit formation has also been genetically engineered in eggplant by using the DefH9-iaaM gene. The DefH9-iaaM gene codes for tryptophan monoxygenase and confers auxin synthesis, while the DefH9 controlling regions drive expression of the gene specifically in the ovules and placenta. This leads to a significant increase in fruit production concomitant with a reduction in cultivation costs. However, in many countries genetically modified crops are not well accepted.

Besides the above described drawbacks of the current parthenocarpic eggplants and methods available, there is another issue. An eggplant that possesses the trait parthenocarpic fruit formation can still produce fruits that contain seeds if the eggplant was able to self-pollinate in certain conditions. The quality of the eggplant fruits can be negatively influenced by the presence of seeds. As a consequence, in case one desires guaranteed seedless pepper fruit, manual emasculation (removal of anthers before maturation) of the pepper plant flowers is a necessity even if the plant itself is parthenocarpic.

The prevention of self-pollination is also an issue in the production of F1 hybrid seeds. The flowers of eggplants are complete, containing both female and male structures, and may be self-pollinated or cross-pollinated. This self-pollination is non-desirable in F1 hybrid seed production, because F1 hybrid seed is produced after crossing of two different plant lines. The unwanted self-pollination can be controlled by laborious manual emasculation. This emasculation is done to prevent a plant from producing pollen so that it serves only as a female parent. Emasculation is time- and cost consuming and thus undesirable.

Another approach for producing seedless eggplant fruits is the use of triploid eggplants. Triploid eggplant exist that can produce seedless eggplant fruits (see WO2009/095266). A triploid eggplant is produced by first crossing a tetraploid eggplant parent plant with another diploid eggplant and then selecting from the population of progeny plants the triploid plants. Preferably, the tetraploid parent is the mother plant and the diploid parent is the father plant. To obtain tetraploid parent plants, common diploid eggplants are given a colchicine treatment. The process of producing a triploid eggplant is laborious and bound by certain treatments.

Citation or identification of any document in this application is not an admission that such document is available as prior art to the present invention.

SUMMARY OF THE INVENTION

It is the object of the present invention to provide an eggplant that can produce fertilization independent seedless fruits and that does not have any of the above stated drawbacks.

The current invention relates to an eggplant (Solanum melongena L.) that shows a combination of both parthenocarpic fruit formation and cytoplasmic male sterility (CMS).

The plant of the invention is a parthenocarpic plant that is unable to produce viable pollen. Since this male-sterile plant can thus not self-pollinate, seed formation is dependent upon pollen from another plant acting as a male plant in the cross. This way the occurrence of selfed progeny in F1 hybrid seed production is avoided. The use of a female sterile plant would not have the same benefits as male sterile plants in F1 hybrid seed production as emasculation would still be necessary.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Eggplant seeds that carry the combined genetic information for parthenocarpic fruit formation and CMS were deposited on 20 Sep. 2012 with the NCIMB, Ferguson Building, Craibstone Estate, Bucksburn, Aberdeen AB21 9YA, UK under accession number NCIMB 42053.

The Deposits with NCIMB, under deposit accession number NCIMB 42053 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

Accordingly, the deposit has been ACCEPTED.

BRIEF DESCRIPTION OF THE DRAWINGS

The following detailed description, given by way of example, but not intended to limit the invention solely to the specific embodiments described, may best be understood in conjunction with the accompanying drawings.

FIG. 1: Flowers with non-opening anthers of CMS plants versus flowers with normally opening anthers of non-CMS plants.

DETAILED DESCRIPTION OF THE INVENTION

The invention relates in particular to eggplant seed capable of growing into a plant that is cytoplasmic male sterile and capable of producing eggplant fruits without fertilization, which seed is obtainable by crossing a mother plant of NCIMB 42053 with a father plant that is optionally parthenocarpic.

Said eggplant seed can also be obtained by crossing a mother plant of NCIMB 42053 with a father plant, that is optionally parthenocarpic, and after this first cross repeatedly backcrossing the progeny plants with the recurrent father plant. By repeatedly backcrossing progeny plants with the recurrent father plant, it is possible to obtain eggplant plants that have the desirable traits or combinations of traits similar to the father plant plus the combined traits of cytoplasmic male sterility and parthenocarpic fruit formation. The invention also relates to the plants that can be grown from these seeds.

According to the invention different combinations of female and male parents could lead to a plant of the invention. However, because cytoplasmic male sterility (CMS) is transferred via the cytoplasm, this trait obviously can only be inherited via a plant acting as a female. To obtain a plant according to the current invention, the plant used as a female in the cross for obtaining the plant with the combination of CMS and parthenocarpic fruit formation in the crossing must always have the trait CMS. The parthenocarpic fruit formation is a trait that can be inherited both from male and female parent plants. To obtain a plant according to the invention as described above, one or both parent plants must have the trait parthenocarpic fruit formation.

The plant that functions as a mother plant in the cross that leads to seed of the invention, can be a plant which representative seed was deposited with the NCIMB under accession number NCIMB 42053. It could also be a plant derived from the plant of which representative seed was deposited under accession number NCIMB 42053 or a plant that has at least the same cytoplasmic male sterility as in a plant of which representative seed was deposited with the NCIMB under accession number NCIMB 42053.

The invention also relates to an eggplant grown from said seed, which plant is cytoplasmic male sterile and capable of producing eggplant fruits without fertilization. Furthermore, said eggplant, which is male sterile and capable of producing eggplant fruits without fertilization, grown from said seed does not show any negative pleiotropic effects.

Moreover, the invention provides a seedless eggplant fruit produced from an eggplant that is cytoplasmic male sterile and capable of producing fruits without fertilization.

This seedless eggplant fruit produced by a male sterile eggplant capable of producing fruits without fertilization, does not show any negative pleiotropic effects, in particular a hollow core and/or a deformed shape.

Furthermore, said seedless eggplant fruit has one or more of the following characteristics: a) a size that is the same or similar to the size of a fruit produced through fertilization; b) a coloration and ripening process that is the same or similar to the coloration and ripening process of a fruit produced through fertilization.

The said seedless eggplant fruit can be the fruit itself, or a product or food product made of the fruit or made of parts thereof, or a processed food product made thereof, and is harvested from an eggplant of the invention or an eggplant grown from seed of the invention which may comprise the combination of parthenocarpic fruit formation and cytoplasmic male sterility.

The invention also relates to progeny of an eggplant as described above that has retained the cytoplasmic male-sterility and the capability of fertilization independent fruit formation of the parent. The cytoplasmic male sterility in said progeny of a plant of the invention is as found in seeds of which a representative sample was deposited under accession number NCIMB 42053. This applies both to the phenotype and the genotype, i.e. the genes underlying the CMS.

The invention further relates to propagation material derived from a plant of the invention or a plant grown from seed of the invention. An eggplant grown from said propagation material, has retained the cytoplasmic male-sterility and the capability of fertilization independent fruit formation. The trait cytoplasmic male sterility in said propagation material derived from a plant of the invention or a plant grown from seed of the invention is as found in seeds of which a representative sample was deposited under accession number NCIMB 42053.

The invention also describes propagation material capable of growing into a plant of the invention or a plant grown from seed of the invention. The propagation material derived from a plant of the invention or capable of growing into a plant of the invention can be selected from a group consisting of: microspores, pollen, ovaries, ovules, embryos, embryo sacs, egg cells, cuttings, roots, stems, cells, protoplasts, leaves, cotyledons, hypocotyls, meristematic cells, roots, root tips, microspores, anthers, flowers, seeds, callus, stems, tissue culture or parts thereof.

In one aspect the invention relates to a method for the production of an eggplant that shows a combination of the traits parthenocarpic fruit formation and cytoplasmic male sterility, which may comprise:

a) crossing a female parent plant which may comprise the trait of cytoplasmic male sterility with another recurrent male parent plant, wherein at least one of the parent plants has the trait of parthenocarpic fruit formation;

b) crossing the resulting F1 with the recurrent parent plant from step a) for obtaining F2 plants;

c) selecting plants that have the combination of cytoplasmic male sterility and parthenocarpic fruit formation in the F2;

d) optionally performing one or more additional rounds of crossing, and subsequently selecting, for a plant which may comprise or show cytoplasmic male sterility and parthenocarpic fruit formation.

The words "trait" and "traits" in the context of this application refer to the phenotype of the plant. In particular, the word "traits" refers to the combination of both parthenocarpic fruit formation and CMS. When a plant shows the trait of the invention, its genome may comprise genetic information causing the trait of the invention.

It is clear that the parent plant that provides the trait of the invention is not necessarily a plant grown directly from the deposited seeds. The parent plant can also be a progeny plant from the seed or a progeny plant from seeds that are identified to have the combination of traits of the invention by other means.

The invention additionally provides a method of introducing other desired traits into an eggplant which shows the combination of the traits parthenocarpic fruit formation and CMS, which may comprise:

a) crossing a first female eggplant that shows a combination of the traits parthenocarpic fruit formation and cytoplasmic male sterility, representative seed of which were deposited under deposit number NCIMB 42053, with a second eggplant that may comprise a desired trait to produce F1 progeny;

b) selecting an F1 progeny that may comprise a combination of said traits plus the desired trait;

c) crossing the selected F1 progeny with the second parent, to produce backcross progeny;

d) selecting backcross progeny which may comprise the desired trait plus the combination of parthenocarpic fruit formation and cytoplasmic male sterility; and e) optionally repeating steps c) and d) one or more times in succession to produce selected fourth or higher backcross progeny that may comprise the desired trait and the combination of said traits. The invention includes an eggplant produced by this method.

Selection for plants having the combination of parthenocarpic fruit formation and cytoplasmic male sterility can be done in the F1 or any further generation by using molecular markers which directly or indirectly detect the genes underlying the traits. In another aspect selection for the trait of the invention is started in the F2 of a cross or alternatively of a backcross. Selection of plants in the F2 can be done phenotypically as well as by using marker(s) which directly or indirectly detect the genes underlying the traits.

In one embodiment selection for plants having the combination of parthenocarpic fruit formation and cytoplasmic male sterility is started in the F3 or a later generation.

In one embodiment the plant which may comprise the traits of parthenocarpic fruit formation and cytoplasmic male sterility is a plant of an inbred line, a hybrid, a doubled haploid, or of a segregating population.

The invention further provides a method for the production of an eggplant having the combination of the traits parthenocarpic fruit formation and cytoplasmic male sterility by using a doubled haploid generation technique to generate a doubled haploid line which may comprise the combination of said traits.

The invention furthermore relates to hybrid seed that can be grown into a plant having the combination of the traits parthenocarpic fruit formation and cytoplasmic male sterility and to a method for producing such hybrid seed which may comprise crossing a first parent plant with a second parent plant and harvesting the resultant hybrid seed, wherein said first parent plant and/or said second parent plant is the plant as claimed.

In one embodiment, the invention relates to a method for producing a hybrid eggplant that has the combination of the traits parthenocarpic fruit formation and cytoplasmic male sterility, which may comprise crossing a first parent eggplant with a second parent eggplant and harvesting the resultant hybrid seed, of which the first parent plant and/or the second parent plant has a combination of both parthenocarpic fruit formation and CMS, and growing said hybrid seeds into hybrid plants having a combination of parthenocarpic fruit formation and CMS.

In another embodiment, the invention relates to a method for producing a hybrid eggplant that has the combination of the traits parthenocarpic fruit formation and cytoplasmic male sterility, which may comprise crossing a first parent eggplant with a second parent eggplant and harvesting the resultant hybrid seed, in which the female parent plant has the trait cytoplasmic male sterility and at least one of the two parents has the trait parthenocarpic fruit formation, and growing said hybrid seeds into hybrid plants having the combination of the traits parthenocarpic fruit formation and cytoplasmic male sterility.

The invention also relates to a method for the production of an eggplant having the combination of parthenocarpic fruit formation and cytoplasmic male sterility by using a seed that may comprise the combination of the traits parthenocarpic fruit formation and CMS for growing the said eggplant. The seeds are suitably seeds of which a representative sample was deposited with the NCIMB under deposit number NCIMB 42053.

The invention also relates to a method for seed production which may comprise growing eggplants from seeds of which a representative sample was deposited with the NCIMB under deposit number NCIMB 42053, allowing the plants to produce seeds, and harvesting those seeds. Production of the seeds is suitably done by crossing.

In one embodiment, the invention relates to a method for the production of an eggplant having a combination of parthenocarpic fruit formation and CMS, by using tissue culture.

The invention furthermore relates to a method for the production of an eggplant having a combination of parthenocarpic fruit formation and CMS by using vegetative reproduction.

The starting materials for tissue culture and vegetative reproduction are suitably plants of the invention, in particular plants grown from seeds of NCIMB 42053 or progeny thereof, or plants that have the CMS of the deposited seeds and another parthenocarpy.

In one embodiment, the invention relates to a method for the production of an eggplant having a combination of parthenocarpic fruit formation and CMS by using a method for genetic modification to introgress the said traits into the eggplant. Genetic modification may comprise transgenic modification or transgenesis, using a gene from a non-crossable species or a synthetic gene, and cisgenic modification or cisgenesis, using a natural gene, coding for a (agricultural) trait, from the crop plant itself or from a sexually compatible donor plant.

The invention also relates to a breeding method for the development of eggplants that have a combination of parthenocarpic fruit formation and CMS wherein germplasm which may comprise said trait is used. Representative seed of said plant which may comprise the combination of parthenocarpic fruit formation and CMS and being representative for the germplasm was deposited with the NCIMB under deposit number NCIMB 42053.

In a further embodiment the invention relates to a method for the production of an eggplant having a combination of parthenocarpic fruit formation and CMS wherein progeny or propagation material of a plant which may comprise the combination of said traits is used as a source to introgress the combination of said traits into another eggplant. Representative seed of said plant which may comprise the combination of parthenocarpic fruit formation and CMS was deposited with the NCIMB under deposit number NCIMB 42053.

The invention provides preferably an eggplant having a combination of parthenocarpic fruit formation and CMS, which plant is obtainable by any of the methods herein described and/or familiar to the skilled person.

The invention relates to a cell of an eggplant, which eggplant may comprise a combination of parthenocarpic fruit formation and CMS, as found in an eggplant grown from seed as deposited with the NCIMB under the accession number NCIMB 42053.

Another embodiment of the invention relates to a cell of an eggplant, which eggplant may comprise a combination of parthenocarpic fruit formation and CMS, as found in an eggplant grown from seed as deposited with the NCIMB under the accession number NCIMB 42053, which eggplant is obtainable by crossing an eggplant with an eggplant grown from seed as deposited with the NCIMB under the accession number NCIMB 42053, and selecting for an eggplant that is capable of parthenocarpic fruit formation and is cytoplasmic male sterile.

Although the cell in itself is not capable of showing the phenotype of the invention it does carry the genetic information that is responsible for the cytoplasmic male sterility and the parthenocarpy, and is as such part of this invention.

The invention also relates to use of seeds that were deposited with the NCIMB under the accession number NCIMB 42053, for transferring the combination of traits parthenocarpic fruit formation and CMS, into another eggplant.

In another embodiment, the invention also relates to the use of an eggplant that may comprise the combination of the traits parthenocarpic fruit formation and CMS, as found in an eggplant grown from seed as deposited with the NCIMB under the accession number NCIMB 42053, as a crop.

Furthermore the invention relates to the use of an eggplant which may comprise the combination of the traits parthenocarpic fruit formation and CMS, as found in an eggplant grown from seed as deposited with the NCIMB under the accession number NCIMB 42053, as a source of seed.

The invention further relates to the use of an eggplant which may comprise the combination of the traits parthenocarpic fruit formation and CMS, as found in an eggplant grown from seed as deposited with the NCIMB under the accession number NCIMB 42053, as a source of propagating material.

Another aspect of the invention relates to the use of an eggplant which may comprise the combination of parthenocarpic fruit formation and CMS, as found in an eggplant grown from seed as deposited with the NCIMB under the accession number NCIMB 42053, for consumption.

Furthermore, the invention relates to the use of combined parthenocarpic fruit formation and CMS eggplant alleles as found in eggplant seeds that were deposited with the NCIMB under the accession number NCIMB 42053, for conferring a combination of parthenocarpic fruit formation and CMS, on an eggplant.

Moreover, the invention relates to the use of an eggplant as a recipient of the combined parthenocarpic fruit formation and CMS eggplant alleles as found in seeds that were deposited with the NCIMB under accession number NCIMB 42053.

In a further embodiment the invention relates to a method for selecting a plant having one or more of the parthenocarpic fruit formation and CMS eggplant alleles as found in seeds that were deposited with the NCIMB under accession number NCIMB 42053 which may comprise screening for the presence of the alleles.

In another embodiment, the invention provides a method for selecting a plant having alleles that confer either or both the traits of CMS and parthenocarpic fruit formation, wherein the alleles are as present in seeds that were deposited with the NCIMB under accession number NCIMB 42053, wherein the screening is done by optical inspection of flowers for showing non-opening anthers and/or seedless fruits in the absence of fertilization.

Use of alleles that cause parthenocarpic fruit formation and/or CMS for the production of a plant being male sterile and/or producing seedless fruits caused by said alleles, wherein the alleles are as found in seeds that were deposited with the NCIMB under accession number NCIMB 42053.

In the present application the terms "parthenocarpy" and "fertilization independent fruit formation" are used interchangeably.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Identification of Eggplants which have Obtained the Combination of CMS and Fertilization Independent Fruit Formation Eggplant seeds from an internal line were germinated and were grown into small plantlets. Subsequently, randomly chosen plants were transferred to a greenhouse in which they were raised according to common eggplant cultivation practice. Measures were taken to prevent any insects from outside entering the greenhouse, so cross-pollination between plants was prevented. The eggplants were monitored on a regular basis in order to visually determine which flowers show non-opening anthers which indicates the CMS trait is present in the plant.

Flowers with non-opening anthers of CMS plants versus flowers with normally opening anthers of non-CMS plants are shown in FIG. 1. Subsequently, the fruits on the eggplants were monitored on fertilization independent (parthenocarpic) fruit formation. A few criteria were important to select the preferred plants.

The fruits were harvested and opened to check if no seeds had formed and to check whether the fruits were normally filled with fruit flesh. The formation of these fruits without seeds should have a size similar to a normal seeded fruit growing on plants with a similar genetic background. The preferred plants had flowers with non-opening anthers and produced fruits containing no seeds and having a fruit size and fruit form similar to a normal seeded fruit growing on plants with a similar genetic background.

Example 2

Introgression of the Combination of the Traits of Cytoplasmic Male Sterility (CMS) and Parthenocarpic Fruit Formation To demonstrate that the combination of CMS and parthenocarpic fruit formation of the invention can be introduced into other eggplant types as well, backcrosses were made with eggplant lines, like the female parent of the variety Nilo RZ F1 as recurrent parent. The plants of the invention, having the combination of traits of CMS and parthenocarpic fruit formation were used as mother plants in these crosses. The resulting F1 and/or F2 progeny produced fruits without fertilization, these fruits contained no seeds and were similar in appearance and characteristics as compared to fruits grown from fertilized flowers of the same plant, under standard Dutch glasshouse conditions.

The invention is further described by the following numbered paragraphs:

1. Eggplant seed capable of growing into a plant that is cytoplasmic male sterile and capable of producing eggplant fruits without fertilization, which seed is obtainable by crossing a mother plant of NCIMB 42053 with a father plant that is optionally parthenocarpic.
2. Plant grown from seed of paragraph 1, which plant is cytoplasmic male sterile and capable of producing eggplant fruits without fertilization.
3. Seedless fruit from a plant of paragraph 2.
4. Fruit of paragraph 3, wherein the fruit does not show negative pleiotropic effects, in particular hollow core and/or deformed shape.
5. Fruit of paragraph 3 or 4, wherein the fruit has one or more of the following characteristics:
    a) a size that is similar to the size of a fruit produced after fertilization;
    b) a coloration and ripening process that is similar to the coloration and ripening process of a fruit produced through fertilization.
6. Progeny of an eggplant of paragraph 2 that has retained the cytoplasmic male-sterility and capability of fertilization independent fruit formation as found in the parent plant.
7. Propagation material derived from a plant of paragraph 2 that has cytoplasmic male-sterility and the capability of fertilization independent fruit formation.
8. Propagation material capable of growing into a plant of paragraph 2, wherein the plant has cytoplasmic male-sterility and the capability of fertilization independent fruit formation.
9. Progeny of paragraph 6 or propagation material of paragraph 7 or 8, wherein the cytoplasmic male sterility is as found in seeds of which a representative sample was deposited under accession number NCIMB 42053.
10. Propagation material of paragraph 7 and 8 wherein the propagation material is selected from the group consisting of: microspores, pollen, ovaries, ovules, embryos, embryo sacs, egg cells, cuttings, roots, stems, cells, protoplasts, leaves, cotyledons, hypocotyls, meristematic cells, roots, root tips, microspores, anthers, flowers, seeds, callus and stems or tissue culture or parts thereof.

11. Eggplant fruit, of paragraph 3-5, or a food product made of a fruit or made of parts thereof, or a processed food product made thereof, wherein the fruit is harvested from an eggplant of paragraph 2.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An eggplant seed capable of growing into a plant that is cytoplasmic male sterile and which plant produces eggplant fruit without fertilization, which seed is the result of a cross between a mother plant and a father plant that is optionally parthenocarpic, wherein the mother plant is a plant grown from seeds of deposit NCIMB 42053, wherein the mother plant is cytoplasmic male sterile and produces eggplant fruit without fertilization; and wherein the fruit of the plant grown from said seed do not show negative pleiotropic effects.

2. A plant grown from the seed as claimed in claim 1, which plant is cytoplasmic male sterile and produces eggplant fruits without fertilization.

3. A seedless fruit from the plant as claimed in claim 2.

4. The fruit as claimed in claim 3, wherein the fruit of the plant grown from said seed do not show the negative pleiotropic effects of a hollow core or a deformed shape.

5. A propagation material from a plant as claimed in claim 2, wherein said propagation material comprises at least one cell of the plant of claim 2, wherein a plant propagated from said material is cytoplasmic male sterile and produces eggplant fruit without fertilization, and wherein the propagation material is cuttings, roots, root tips, stems, leaves, cotyledons, hypocotyls or meristematic cells; or parts thereof; or cells, protoplasts, callus or tissue culture thereof.

6. An eggplant fruit as claimed in claim 3, or a food product made of an eggplant fruit as claimed in claim 3, or a food product made of parts of an eggplant fruit as claimed in claim 3, wherein said food product comprises at least one cell of the fruit of claim 3.

* * * * *